United States Patent
Setsukinai et al.

(10) Patent No.: US 7,378,282 B2
(45) Date of Patent: May 27, 2008

(54) METHOD FOR MEASURING HYPOCHLORITE ION

(75) Inventors: Ken-ichi Setsukinai, Tokyo (JP);
Yasuteru Urano, Kanagawa (JP);
Tetsuo Nagano, 1-28-15, Amanuma,
Suginami-ku, Tokyo 167-0032 (JP)

(73) Assignees: Tetsuo Nagano, Tokyo (JP); Daiichi Pure Chemicals Co., Ltd., Tokyo (JP)

( * ) Notice: Subject to any disclaimer, the term of this patent is extended or adjusted under 35 U.S.C. 154(b) by 585 days.

(21) Appl. No.: 10/437,437

(22) Filed: May 14, 2003

(65) Prior Publication Data
US 2004/0229371 A1 Nov. 18, 2004

(51) Int. Cl.
*G01N 33/00* (2006.01)
*G01N 21/76* (2006.01)

(52) U.S. Cl. .................. 436/128; 436/172; 436/91; 436/124

(58) Field of Classification Search ................ 436/128, 436/172, 91, 124
See application file for complete search history.

(56) References Cited

U.S. PATENT DOCUMENTS

| | | |
|---|---|---|
| 5,623,080 A | 4/1997 | Neckers et al. |
| 6,525,088 B1 | 2/2003 | Nagano et al. |
| 7,087,766 B2 * | 8/2006 | Nagano et al. ............. 549/223 |

FOREIGN PATENT DOCUMENTS

| | | |
|---|---|---|
| EP | 0515133 | 11/1992 |
| EP | 1260508 A1 * | 11/2002 |
| JP | 60-54381 | 3/1985 |
| WO | 01/62755 | 8/2001 |
| WO | 01/63265 | 8/2001 |
| WO | 01/64664 | 9/2001 |

OTHER PUBLICATIONS

Program and Abstracts of the 24th Congress of the Society for Free Radical Research Japan, pp. 36, May 18-19, 2002, accompanied by an English language translation.
Ken-Ichi Setsukinai et al., "Development of Novel Reliable Fluorescence Probes to Detect Reactive Oxygen Species which can Distinguish Specific Species", Free Radical Biology & Medicine, vol. 33 (Supplement 2), pp. S425 (2002).
Ken-Ichi Setsukinai et al., "Development of Novel Reliable Fluorescence Probes to Detect Reactive Oxygen Species which can Distinguish Specific Species", The Journal of Biological Chemistry, vol. 278, No. 5, pp. 3170-3175 (2003).
Seymour J. Klebanoff et al., "The Neutrophil: Function and Clinical Disorders", North -Holland Publishing Company, Amsterdam, pp. xi-xiv, 409-488 (1978).
Makoto Suematsu et al., "In Vivo Visualization of Oxyradical-Dependent Photoemission During Endothelium-Granulocyte Interaction in Microvascular Beds Treated with Platelet-Activating Factor", J. Biochem, vol. 106, pp. 355-360 (1989).
Hiroshi Wakeyama et al., "Superoxide-forming NADPH Oxidase Preparation of Pig Polymorphonuclear Leucocytes", Biochem J., vol. 205, pp. 593-601 (1982).
Katsuko Kakinumat et al., "Electron Spin Resonance Studies on a Flavoprotein in Neutrophil Plasma Membranes", The Journal of Biological Chemistry, vol. 261, No. 20, pp. 9426-9432 (1986).
Kabatc, J., et al., Polymer 40(3), pp. 735-745 (1999).
Setsukinai, Ken-ichi, et al., J. Chem. Soc., Perkin Trans. 2, 12, pp. 2453-2457, 2000.
Nagano, T., et al., Free Radicals in Clinical Medicine, vol. 7, pp. 35-41, 1993.
Saito, I., et al., J. Am. Chem. Soc., vol. 107, pp. 6329-6334, 1985.
T. W. Greene et al., Protective Groups in Organic Synthesis, John Wiley & Sons, Inc., 1981, pp. v-xxi and 369-405.
English Language Abstract of JP 60-54381.

* cited by examiner

*Primary Examiner*—Jill Warden
*Assistant Examiner*—Keri A Moss
(74) *Attorney, Agent, or Firm*—Greenblum & Bernstein, P.L.C.

(57) ABSTRACT

A method for measuring hypochlorite ion, which comprises the steps of:
(A) reacting, with hypochlorite ion, a compound represented by the following general formula (I):

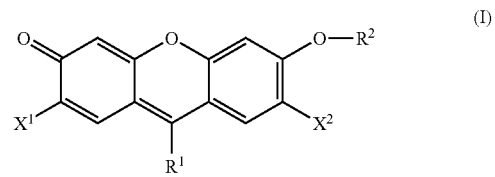

wherein $R^1$ represents a 2-carboxyphenyl group which may be substituted; $R^2$ represents a phenyl group which is substituted with a substituted or unsubstituted amino group; $X^1$ and $X^2$ each independently represents either hydrogen atom or a halogen atom; or a salt thereof; and
(B) measuring fluorescence of a dearylated compound generated in the aforementioned step (A) or a salt thereof.

8 Claims, 1 Drawing Sheet

METHOD FOR MEASURING HYPOCHLORITE ION

TECHNICAL FIELD

The present invention relates to a method for measuring hypochlorite ion. The present invention also relates to an agent for measuring hypochlorite ion and a kit used for said measuring method.

BACKGROUND ART

Hypochlorite ion is one of reactive oxygen species whose function in organisms has recently been focused. It is considered that bactericidal action of neutrophils is mainly derived from hypochlorite ion. Hypochlorite ion has been shown to be generated from hydrogen peroxide and chloride ions by myeloperoxidase in azurophilic granules in vitro (Klebanoff, S. J., and Clark, R. A. (1978) *The Neutrophils: Function and Clinical Disorders*, North-Holland Publishing Company, Amsterdam, Netherlands). In addition, hypochlorite ion is considered to play an important role in injury to the vascular endothelial surface in platelet-activating factor-induced microvascular damage (Suematsu, M., Kurose, I., Asako, H., Miura, S., and Tsuchiya, M. (1989) *J. Biochem.* 106, 355-360). However, it has been difficult to conclude that hypochlorite ion participates directly in the aforementioned mechanism in organisms, because a completely selective measuring method for hypochlorite ion, especially a measuring method in vivo had not been established.

Ten and several methods such as chemiluminescence, electron spin resonance (ESR), and luminescence are known as methods for measuring reactive oxygen species. Among them, the fluorescence detection method is superior from viewpoints of sensitivity and experimental convenience. In the fluorescence detection method, DCFH (2',7'-dichlorodihydrofluorescein) or the like is used as a fluorescence probe for measuring reactive oxygen species. However, DCFH cannot successfully distinguish types of reactive oxygen species, and as a consequence, fails to selectively measure hypochlorite ion.

DISCLOSURE OF THE INVENTION

An object of the present invention is to provide a method for selectively measuring hypochlorite ion. Another object of the present invention is to provide an agent for measuring hypochlorite ion. Further object of the present invention is to provide a kit used for the aforementioned measuring method. Specifically, an object of the present invention is to provide a means that enables measurement of hypochlorite ion localized in specific cells and tissues in organisms.

The inventors of the present invention previously provided non-fluorescent compounds which effectively react with reactive oxygen under physiological conditions to generate dearylated fluorescent compounds, and by using said compounds, they succeeded in a selective and highly sensitive measurement of reactive oxygen localized in living cells and living tissues by fluorescence detection method (WO 01/64664).

On the basis of these compounds, the inventors of the present invention conducted further researches to achieve the foregoing objects, and as a result, they found that hypochlorite ion can be measured by using a compound represented by the following general formula (I) alone, or in a combination with a compound represented by the following general formula (II). The present invention was achieved on the basis of these findings.

The present invention thus provides a measuring method for hypochlorite ion which comprises the following steps:
(A) reacting, with hypochlorite ion, a compound represented by the following general formula (I):

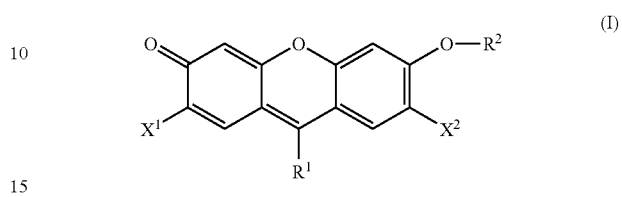

(wherein $R^1$ represents a 2-carboxyphenyl group which may be substituted; $R^2$ represents a phenyl group which is substituted with a substituted or unsubstituted amino group; $X^1$ and $X^2$ each independently represents a hydrogen atom or a halogen atom) or a salt thereof; and
(B) measuring fluorescence of a dearylated compound generated in the aforementioned step (A) or a salt thereof. The present invention also provides an agent for measuring hypochlorite ion which comprises a compound represented by the aforementioned formula (I) or a salt thereof. According to a preferred embodiment, there is provided the agent for measuring hypochlorite ion which comprises the aforementioned compound wherein both of $X^1$ and $X^2$ are hydrogen atoms or a salt thereof.

From another aspect, the present invention provides a measuring method for hypochlorite ion which comprises the following steps of:
(C) reacting a compound represented by the aforementioned general formula (I) or a salt thereof with a reactive species containing oxygen;
(D) reacting a compound represented by the following general formula (II):

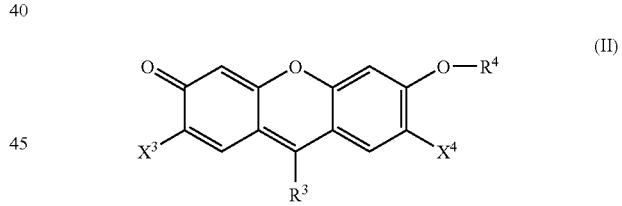

(wherein $R^3$ represents a 2-carboxyphenyl group which may be substituted; $R^4$ represents a hydroxyphenyl group; $X^3$ and $X^4$ each independently represents either hydrogen atom or a halogen atom) or a salt thereof with said reactive species containing oxygen;
(E) measuring fluorescence of a dearylated compound generated in each of the aforementioned processes (C) and (D) or a salt thereof; and
(F) judging that said reactive species containing oxygen is hypochlorite ion when a dearylated compound is generated in the aforementioned process (C) and a dearylated compound is not substantially generated in the aforementioned process (D).

From further aspect, the present invention provides a kit for measuring hypochlorite ion which comprises a compound represented by the aforementioned general formula (I) or a salt thereof and a compound represented by the aforementioned general formula (II) or a salt thereof.

BEST MODE FOR CARRYING OUT THE INVENTION

Figure 1:
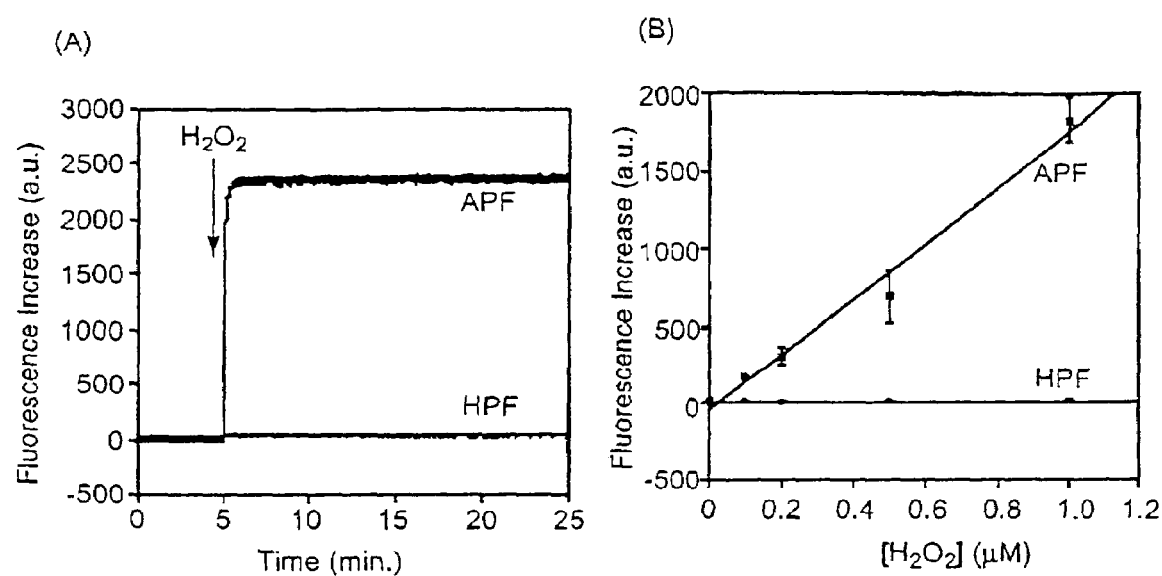
FIG. 1 shows a result of a measurement of hypochlorite ion using HPF and APF.

The compounds represented by the general formula (I) and the compounds represented by the general formula (II) which are used in the measuring method of the present invention are both disclosed in WO 01/64664, and easily prepared by a method disclosed in this publication.

$R^1$ and $R^3$ each represents a 2-carboxyphenyl group which may be substituted, and is preferred to be an unsubstituted 2-carboxyphenyl group.

As $R^2$, a phenyl group substituted with substituted or unsubstituted amino groups can be used. A phenyl group substituted with one substituted or unsubstituted amino group is preferred and a phenyl group substituted with one unsubstituted amino group is more preferred. When the amino group has a substituent, the types of the substituent are not particularly limited. For example, an alkyl group, an alkenyl group, an alkanoyl group, and arylcarbonyl group can be used as a substituent. When the amino group has two or more substituents, they may be the same or different. 4-Aminophenyl group is preferred as $R^2$.

$R^4$ represents a hydroxyphenyl group, and 4-hydroxyphenyl group is preferred.

$X^1$, $X^2$, $X^3$, and $X^4$ each represents either hydrogen atom or a halogen atom. In a compound represented by the general formula (I), $X^1$ and $X^2$ are preferred to be hydrogen atoms, and in a compound represented by the general formula (II), $X^3$ and $X^4$ are preferred to be hydrogen atoms. When $X^1$ and $X^2$ are halogen atoms in a compound represented by the general formula (I), they may be the same or different, and for example, fluorine atom and chlorine atom are preferably used. The same is true when $X^3$ and $X^4$ are halogen atoms in a compound represented by the general formula (II).

Examples of the salt of a compound represented by the general formula (I) or the general formula (II) include a base addition salt, an acid addition salt, and an amino acid addition salt. Examples of a base addition salt include metal salts such as sodium, potassium, calcium, and magnesium; a salt of ammonia; and salts of organic amines such as trimethylamine, piperidine, and morpholine. Examples of an acid addition salt include salts with mineral acids such as hydrochloric acid, sulfuric acid, and nitric acid; salts with organic acids such as methanesulfonic acid, p-toluenesulfonic acid, citric acid, and oxalic acid. An example of an amino acid addition salt includes glycine salt. However, the salts are not limited to the above examples.

Among them, a physiologically acceptable water soluble salt is preferably used for the agent and the measuring method of the present invention. A compound represented by the general formula (I) and the general formula (II) or a salt thereof in a free form may exist as a hydrate or a solvate, which may be used for the method of the present invention. Types of the solvent which forms the solvate are not limited. Such solvents can be exemplified by ethanol, acetone, and isopropanol.

A compound represented by the general formula (I) or (II) may have one or more of asymmetric carbon atoms depending on types of their substituents and stereoisomers such as optical isomers, or diastereoisomers may exist. For the method of the present invention, any of the followings may be used: stereoisomers in a pure form, any mixtures of stereoisomers, racemates and the like. The compound represented by the general formula (I) or (II) may form a lactone ring in the molecule. The compound in which a lactone ring is formed may also be used for the method of the present invention.

The term "measurement" used in the present specification shall be construed in its broadest sense, including quantification, qualification, measurements performed for the purpose of diagnosis, tests, detections and the like.

The first embodiment of the measuring method of the present invention comprises the steps of (A) reacting a compound represented by the general formula (I) or a salt thereof with hypochlorite ion; and (B) measuring fluorescence of a dearylated compound generated in the aforementioned process (A) or a salt thereof. A compound represented by the general formula (I) is featured to have high reactivity to hypochlorite ion, and substantially no reactivity to singlet oxygen, superoxide anion, hydrogen peroxide, or nitric oxide. Therefore, hypochlorite ion contained in samples can be measured by the method of the aforementioned embodiment.

The second embodiment of the measuring method of the present invention comprises the steps of (C) reacting a compound represented by the general formula (I) or a salt thereof with a reactive species containing oxygen; (D) reacting a compound represented by the general formula (II) or a salt thereof with the reactive species containing oxygen; and (E) measuring fluorescence of a dearylated compound generated in the aforementioned processes (C) and (D) or a salt thereof. The term "reactive species containing oxygen" used in the present specification includes hypochlorite ion as well as reactive oxygen species such as hydroxyl radical, singlet oxygen, superoxide anion, hydrogen peroxide, and nitric oxide.

As explained above, a compound represented by the general formula (I) has high reactivity to hypochlorite ion, and substantially no reactivity to singlet oxygen, superoxide anion, hydrogen peroxide, or nitric oxide. However, such a compound may have reactivity to hydroxyl radical. In contrast, the compound represented by the general formula (II) has substantially no reactivity to singlet oxygen, superoxide anion, hydrogen peroxide, nitric oxide, and hypochlorite ion, and has reactivity only to hydroxyl radical. Therefore, in the aforementioned second embodiment, it can be judged that the reactive species containing oxygen subjected to the measurement is hypochlorite ion when a dearylated compound is generated in the aforementioned step (C) and a dearylated compound is not substantially generated in the aforementioned step (D). When dearylated compounds are generated in both of the aforementioned processes (C) and (D), the reactive species containing oxygen subjected to the measurement can be judged hydroxyl radical.

Fluorescence of the dearylated compounds or salts thereof can be measured by an ordinary method. For example, a method of measuring fluorescence spectra in vitro, or a method of measuring fluorescence spectra in vivo by a bioimaging technique can be employed. A compound represented by the general formula (I) or (II) used in the present invention has a feature to be taken up into a cell. Therefore, hypochlorite ion localized in individual cells can be measured with high sensitivity by a bioimaging technique. Using the method of the present invention, hypochlorite ion localized in individual cells and specific tissues can be precisely and easily measured, which enables elucidation of the role of hypochlorite ion in organisms. In addition, diagnoses of specific diseases can be achieved by using the method of the present invention. For example, hypochlorite ion is known to be generated by neutrophils in the presence of *Helicobacter pylori*. Further, diseases wherein neutrophils are involved in an immune reaction are exemplified by bacterial infectious diseases including gastritis, gastroduodenal ulcer, and gastric cancer. The method of the present invention is also useful for convenient and rapid diagnoses of these diseases.

As the agent for measuring hypochlorite ion provided by the present invention, a compound of the aforementioned general formula (I) or a salt thereof, per se, may be used. The agent may also be used as a composition formulated with additives ordinarily used for preparation of reagents, if desired. For example, as additives for a use of the agent under a physiological condition, additives such as dissolving aids, pH adjusters, buffers, isotonic agents and the like can be used, and amounts of these additives can suitably be chosen by those skilled in the art. The compositions may be provided as those in appropriate forms, for example, powdery mixtures, lyophilized products, granules, tablets, solutions and the like.

The kit provided by the present invention, which can be used as a kit to conduct the measuring method according to the aforementioned second embodiment, comprises a compound represented by the aforementioned general formula (I) or a salt thereof and the compound represented by the aforementioned general formula (II) or a salt thereof. Each of the compounds represented by the aforementioned general formula (I) or a salt thereof and the compounds represented by the aforementioned general formula (II) or a salt thereof is provided as an individually packaged form. Each of the packaged forms can be provided as a composition formulated with additives ordinarily used for preparation of reagents, if desired. The additives and compositions are the same as those explained above.

EXAMPLES

The present invention will be explained more specifically by referring to the following examples. However, the scope of the present invention is not limited to the examples.

In the following example, a compound wherein $R^1$ is 2-carboxyphenyl group, and $R^2$ is 4-aminophenyl group in the general formula (I) (hereinafter referred to as "APF") and a compound wherein $R^3$ is 2-carboxyphenyl group, and $R^4$ is 4-hydroxyphenyl group in the general formula (II) (hereinafter referred to as "HPF") were used. Each of HPF and APF is dissolved in dimethylformamide (DMF) to obtain a 10 mM solution, and then added with a 100 mM sodium phosphate buffer (pH 7.4) to obtain a final concentration of 10 µM, unless otherwise specifically mentioned.

Excitation spectra and fluorescence spectra were analyzed with Hitachi F4500. The slit width was 2.5 nm in both of the excitation spectra and fluorescence spectra. The photomultiplier voltage was 950 V. Unless otherwise specifically mentioned, excitation wavelength was 490 nm, fluorescence wavelength was 515 nm, and the measurement was performed at 37° C.

Example 1

Comparison of Reactivity of APF and HPF Between Reactive Species Containing Oxygen Reactivities of APF and HPF to various reactive species containing oxygen were studied. Reactivity of 2',7'-dichlorodihydrofluorescein (DCFH), used as a reference, was studied in a similar manner. For a preparation of DCFH, DCFH-DA (diacetate) was dissolved in DMF to obtain a 10 mM solution, which is further added to an aqueous sodium hydroxide solution (0.01 M) to obtain a 10-fold diluted solution, and the mixture was incubated at 37° C. for 30 minutes under dark condition for deacetylation. The resulting solution was then added to a sodium phosphate buffer (pH 7.4; 0.1M) to obtain a 10 µM solution. The measurement was performed with excitation wavelength at 500 nm and with fluorescence wavelength at 520 nm for DCFH.

(1) Hydroxyl Radical ($^-$OH)

A 10 µM fluorescence probe solution was added with an aqueous hydrogen peroxide solution (a final concentration of 1 mM), and further slowly added with an aqueous ferrous perchlorate (a final concentration of 100 µM). Fluorescence intensities before and after the addition of the hydrogen peroxide solution and the aqueous ferrous perchlorate were measured. The measurement of the fluorescence intensities was performed at room temperature.

(2) Singlet Oxygen ($^1O_2$)

A 10 µM fluorescence probe solution was put in a fluorescence cell, added with 3-(1,4-dihydro-1,4-epidioxy-1-naphthyl)propionic acid (EP-1; a final concentration of 100 µM), and was reacted for 30 minutes. Fluorescence intensities before the addition of EP-1 and 30 minutes after the addition were measured.

(3) Superoxide ($O_2^-$)

A 10 µM fluorescence probe solution was put in a fluorescence cell, added with $KO_2$ (a final concentration of 100 µM), and was reacted for 30 minutes. Fluorescence intensities before the addition of $KO_2$ and 30 minutes after the addition were measured.

(4) Hydrogen Peroxide ($H_2O_2$)

A 10 µM fluorescence probe solution was put in a fluorescence cell, added with $H_2O_2$ (a final concentration of 100 µM), and was reacted for 30 minutes. Fluorescence intensities before the addition of $H_2O_2$ and 30 minutes after the addition were measured.

(5) Nitric Oxide (NO)

A 10 µM fluorescence probe solution was put in a fluorescence cell, added with 1-hydroxy-2-oxo-3-(3-aminopropyl)-3-ethyl-1-triazine ($NOC_{13}$; a final concentration of 100 µM), and was reacted for 30 minutes. Fluorescence intensities before the addition of $NOC_{13}$ and 30 minutes after the addition were measured.

(6) Hypochlorite Ion ($^-$OCl)

A 10 µM fluorescence probe solution was put in a fluorescence cell, added with an aqueous sodium hypochlorite solution (a final concentration of 1.0 µM). Fluorescence intensities before and after the addition of an aqueous sodium hypochlorite solution were measured.

(7) Autoxidation

A 10 µM fluorescence probe solution was put in a fluorescence cell, and was left under a fluorescent lamp for 2.5 hours. Fluorescence intensities before and after being left were measured.

Results are shown in Table 1. DCFH well reacted with each of the reactive oxygen species, and no specificity was observed. In addition, DCFH was susceptible to autoxidation. In contrast, absolutely no autoxidation of APF and HPF was observed. Both of APF and HPF showed high reactivity to hydroxyl radical. APF also showed high reactivity to hypochlorite ion, while HPF had no reactivity to hypochlorite ion.

TABLE 1

| Reactive species containing oxygen | HPF | APF | DCFH |
|---|---|---|---|
| $^-$OH | 730 | 1200 | 7400 |
| $^-$OCl | 6 | 3600 | 86 |
| $^1O_2$ | 5 | 9 | 26 |
| $O_2^-$ | 8 | 6 | 67 |
| $H_2O_2$ | 2 | <1 | 190 |
| NO | 6 | <1 | 150 |
| Autoxidation | <1 | <1 | 2000 |

Example 2

Application to Myeloperoxidase/$H_2O_2$ System (A) By using a 100 mM sodium phosphate buffer (pH 7.4) containing 150 mM sodium chloride, a 10 μM HPF solution and a 10 μM APF solution were prepared. Myeloperoxidase (human) were added to these solutions to obtain a final concentration of 11.2 nM. Each of the solution was put in each fluorescence cell, and a change in the fluorescence intensity with passeage of time was measured. The temperature of the solutions were set at 37° C. About 5 minutes after the start of the measurement, hydrogen peroxide was added to obtain a final concentration of 1 μM. As clearly shown in FIG. 1(A), by the addition of hydrogen peroxide, an increase in the fluorescence intensity was not observed in HPF, while a significant increase in the fluorescence intensity was observed in APF.

(B) By using a 100 mM sodium phosphate buffer (pH 7.4) containing 150 mM sodium chloride, a 10 μM HPF solution and a 10 μM APF solution were prepared. Myeloperoxidase (human) were added to these solutions to obtain a final concentration of 11.2 nM. Each of the solutions was put in each fluorescence cell and a fluorescence intensity was measured at 37° C. Then, hydrogen peroxide was added to each solution to obtain final concentrations of 0.1 μM, 0.2 μM, 0.5 μM, and 1.0 μM. The solutions were left with stirring for 5 minutes, and the fluorescence intensity was measured again after the 5 minutes. A correlation between a concentration of hydrogen peroxide and an increase in the fluorescence intensity before and after the addition of hydrogen peroxide is shown in FIG. 1(B). No increase in the fluorescence intensity was observed for HPF. Whilst, for APF, fluorescence intensity was increased in a manner dependent on the concentration of the added hydrogen peroxide.

Since an increase in the fluorescence intensity by APF was observed, while no increase in the fluorescence intensity by HPF was observed, the target reactive species containing oxygen was identified as hypochlorite ion. It can be concluded that hypochlorite ions, generated by the oxidation of chloride ions with the addition of hydrogen peroxide in the presence of Myeloperoxidase, were detected by APF. Since the measurement of hypochlorite ion by APF is highly sensitive, the measurement was free from the effect of a slightly detected fluorescence increase caused by an addition of hydrogen peroxide. In addition, the measured increase of fluorescence was dependent on the concentration of the added hydrogen peroxide.

Example 3

Fluorescence Imaging of Neutrophils

According to the method described in Wakeyama, H., Takeshige, K., Takayanagi, R., and Minakami S. (1982) Biochem. J. 205, 593-601 and Kakinuma, K., Kaneda, M., Chiba, T., and Ohnishi, T. (1986) J. Biol. Chem. 261, 9426-9432, neutrophils were obtained from 1.8 liters of porcine blood. Erythrocytes in the buffy coat collected from the blood were hemolyzed with a large volume of an ice-cooled 0.2% aqueous sodium chloride solution for 30 minutes and then the preparation was promptly mixed with an equal volume of a 1.6% aqueous sodium chloride solution to restore the isotonic condition. Neutrophils were separated from platelets and mononuclear cells by the Conrey-Ficoll method. The neutrophils were suspended in Krebs Ringer phosphate buffer (114 mM NaCl, 4.6 mM KCl, 2.4 mM $MgSO_4$, 1.0 mM, $CaCl_2$, 15 mM $NaH_2PO_4/Na_2HPO_4$, pH7.4).

The separated neutrophils were seeded onto a glass-bottomed dish. Then the cells were loaded with HPF or APF (10 μM) after incubation for 30 minutes at room temperature. These neutrophils were stimulated with 4β-phorbol-12-myristate-13-acetate (PMA) (2 ng/mL). Fluorescence imaging was measured twice in each experiment: one is before and the other is 10 minutes after the stimulation with PMA. For the measurement, LSM510 cofocal laser scanning unit (Carl Zeiss Co., Ltd.) coupled with an Axiovert 100M inverted microscope with a Plan-Neofluar 100×/1.3 objective lens (Carl Zeiss Co., Ltd.) was used. The excitation wavelength was 488 nm, and the emission was filtered using a 505-550 nm barrier filter. In HPF-loaded neutrophils, no difference was observed in fluorescence intensity before and after the stimulation with PMA, while in APF-loaded neutrophils, a significant increase was observed in fluorescence intensity after stimulation with PMA. From these results, the reactive species containing oxygen generated by the stimulation with PMA was shown to be hypochlorite ion in vivo.

INDUSTRIAL APPLICABILITY

The method for measuring hypochlorite ion of the present invention is useful, in particular, as a method for precisely and conveniently measuring hypochlorite ion localized in specific cells and tissues in organisms by a bioimaging technique. In addition, a sole participation of hypochlorite ion, among various reactive species containing oxygen, can be clearly verified by using the method of the present invention.

What is claimed is:

1. A method for measuring hypochlorite ion which comprises:
    (A) reacting a compound represented by the following general formula (I) or a salt thereof with hypochlorite ion to generate a dearylated compound, the compound of general formula (I) or salt thereof having high reactivity to hypochlorite ion and substantially no reactivity to singlet oxygen, superoxide anion, hydrogen peroxide or nitric oxide:

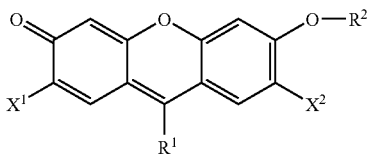

(I)

wherein $R^1$ represents a 2-carboxyphenyl group which may be substituted; $R^2$ represents a phenyl group which is substituted with a substituted or unsubstituted amino group; $X^1$ and $X^2$ each independently represents hydrogen atom or a halogen atom; and (B) measuring fluorescence of the dearylated compound or a salt thereof to provide measurement of hypochlorite ion even in the presence of any singlet oxygen, superoxide anion, hydrogen peroxide and nitric oxide.

2. The method according to claim 1 wherein the hypochlorite ion is localized in cells.

3. The method according to claim 1 wherein $R^2$ is 4-aminophenyl group.

4. A method for measuring hypochlorite ion which comprises:

(A) reacting a compound represented by the following general formula (I) or a salt thereof with a reactive species containing oxygen:

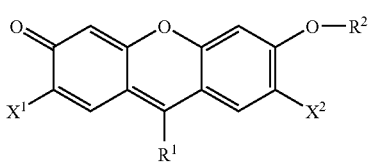

(I)

wherein $R^1$ represents a 2-carboxyphenyl group which may be substituted; $R^2$ represents a phenyl group which is substituted with a substituted or unsubstituted amino group; $X^1$ and $X^2$ each independently represents hydrogen atom or a halogen atom;

(B) reacting a compound represented by the following general formula (II):

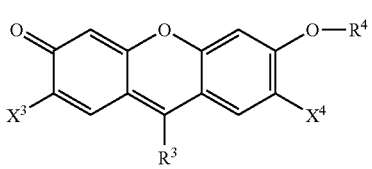

(II)

wherein $R^3$ represents a 2-carboxyphenyl group which may be substituted; $R^4$ represents a hydroxyphenyl group; $X^3$ and $X^4$ each independently represents hydrogen atom or a halogen atom; or a salt thereof with said reactive species containing oxygen;

(C) measuring fluorescence of a dearylated compound generated in each of the aforementioned processes (A) and (B) or a salt thereof and (D) judging that said reactive species containing oxygen is hypochlorite ion when a dearylated compound is generated in the aforementioned (A) and a dearylated compound is not substantially generated in the aforementioned (B).

5. The method according to claim 4 wherein the hypochlorite ion is localized in cells.

6. The method according to claim 4 wherein $R^2$ is 4-aminophenyl group.

7. The method according to claim 6 wherein $R^4$ is 4-hydroxyphenyl group.

8. The method according to claim 4 wherein $R^4$ is 4-hydroxyphenyl group.

* * * * *

UNITED STATES PATENT AND TRADEMARK OFFICE
CERTIFICATE OF CORRECTION

PATENT NO. : 7,378,282 B2 Page 1 of 1
APPLICATION NO. : 10/437437
DATED : May 27, 2008
INVENTOR(S) : K. Setsukinai It is certified that error appears in the above-identified patent and that said Letters Patent is hereby corrected as shown below:

At column 10, line 24 (claim 4, line 22) of the printed patent, after "thereof" insert -- ; --.

Signed and Sealed this

Sixth Day of January, 2009

JON W. DUDAS
*Director of the United States Patent and Trademark Office*